US00PP37360P2

(12) United States Plant Patent
Hansen

(10) Patent No.: US PP37,360 P2
(45) Date of Patent: Apr. 7, 2026

(54) ***ECHINACEA* PLANT NAMED 'Knock 'em Red'**

(50) Latin Name: ***Echinacea* hybrid**
Varietal Denomination: Knock 'em Red

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,867

(22) Filed: Oct. 14, 2025

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

*Primary Examiner* — Susan McCormick Ewoldt

(57) ABSTRACT

The new and distinct cultivar of *Echinacea* plant named 'Knock 'em Red' with fragrant inflorescences on strong well-branched stems above dark green foliage. The inflorescences produce single whorls of long, broad, overlapping, mostly-horizontal, lightly sweet, bright crimson ray florets that change with maturity to more reddish and then mauve before dehiscing. The new plant is vigorous and produces a compact habit and flowers from mid-summer to fall frost. The new plant is attractive and suitable as a potted plant, for the landscape, and for cut flower arrangements.

2 Drawing Sheets

Botanical denomination: *Echinacea* hybrid.
Cultivar designation: 'Knock 'em Red'.

STATEMENT REGARDING PRIOR DISCLOSURES UNDER 37 CFR 1.77(B)(6)

The first offer for sale of the claimed plant was to North Coast Perennials by Walters Gardens, Inc. on Oct. 15, 2024. *Echinacea* 'Knock 'em Red' was also listed with a photograph and brief description on a website operated by Walters Gardens, Inc. on Dec. 1, 2024, and the "Walters Gardens 2025-2026 Catalog" distributed first on Jun. 3, 2025. Walters Gardens, Inc. obtained the plant and all information relating thereto from the inventor. No plants of *Echinacea* 'Knock 'em Red' have been sold in this country or anywhere in the world nor has any disclosure of the new plant been made more than one year prior to the filing date of this application and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Knock 'em Red'. The new plant was the result of a cross in the summer of 2018, by the inventor at a wholesale perennial nursery in Zeeland, Michigan between the proprietary unreleased hybrid known only by the breeder code as 17-7-x (not patented) and the proprietary unreleased hybrid known only by the breeder code as 17-7-xx (not patented) at a wholesale perennial nursery in Zeeland, Michigan. This single seedling selected was evaluated first in trials in the summer of 2019 at the same nursery and assigned the breeder code of 18-33-10. *Echinacea* 'Knock 'em Red' has been asexually propagated at the same nursery by basal crown division since 2020 and also using careful shoot tip tissue culture procedures at the same nursery and both propagation methods have been found to reproduce plants that exhibit all the characteristics identical to the original plant.

*Echinacea* 'Knock 'em Red' is distinct from all other Coneflowers known to the inventor. The nearest comparison cultivars are: 'Dixie Scarlet' U.S. Plant Pat. No. 26,110, 'Embers Fever' U.S. Plant Pat. No. 31,466, 'Fatal Attraction' U.S. Plant Pat. No. 18,429, and 'Hot Papaya' U.S. Plant Pat. No. 21,022, and 'Raspberry Truffle' U.S. Plant Pat. No. 22,612.

'Dixie Scarlet' has a shorter habit, smaller inflorescences, fewer, thinner, and less imbricate ray florets. 'Embers Fever' is slightly shorter in habit, with much less branching, and the ray florets are more reddish. 'Fatal Attraction' is slightly smaller in habit and more upright and less mounded, smaller inflorescences with ray florets of dark purplish-red. 'Hot Papaya' has a taller and narrower habit, fewer ray petals per inflorescence that a lighter orangish color.

The female parent plant, 17-7-x, is taller with more branching, with larger and wider petals of fuchsia pink. The male parent plant, 17-7-xx, is a sibling to the female parent and has a shorter habit with less basal branching, and the flower color is more true reddish colored.

SUMMARY OF THE INVENTION

*Echinacea* 'Knock 'em Red' has not been evaluated under all possible environmental conditions. The phenotype may vary with variations in environment including: temperature, available sunlight intensity and duration, nutrients, water, etc. without a change in the genotype of the plant. The new plant is distinct from its parents and all other *Echinacea* known to the applicant in the following combined traits:

1. Large, broad, sweetly fragrant inflorescences with single whorl of ray florets that stay mostly horizontal once open;

2. Numerous ray petals in a single row are wide and broadly-overlapping;
3. Ray petals begin bright crimson and lighten with maturity to more reddish and then mauve before dehiscing;
4. Vigorous growth and excellent habit with extensive branching;
5. Large, dark-green, lanceolate foliage.

BRIEF DESCRIPTION OF THE DRAWINGS

The photographs of 'Knock 'em Red' demonstrate the overall appearance of the plant including the unique traits. The drawings of the new plant are of a two-year-old plant grown in full-sun trial garden in Zeeland, Michigan. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
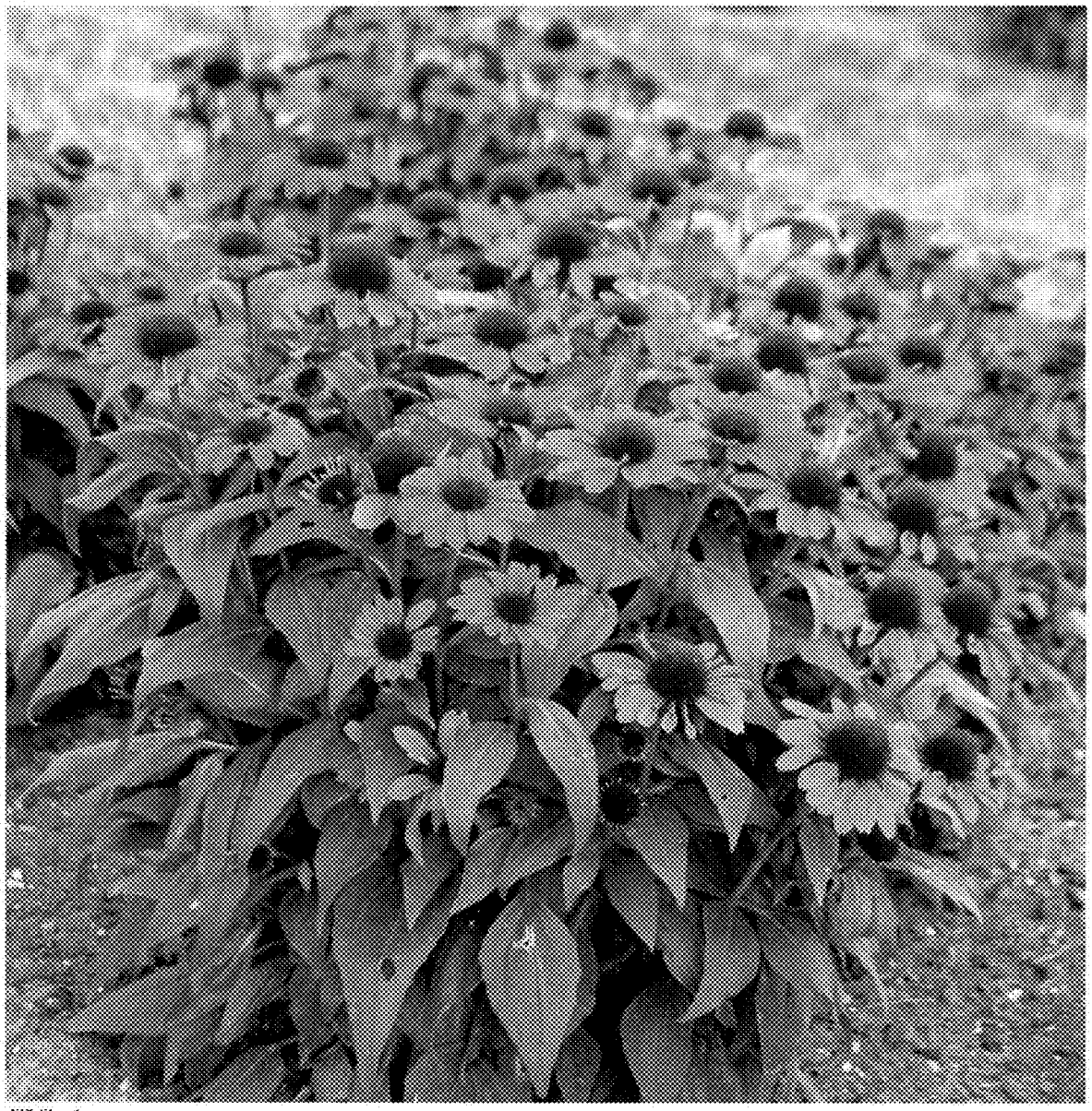
FIG. 1 shows the habit of the new plant in flower.
Figure 2:
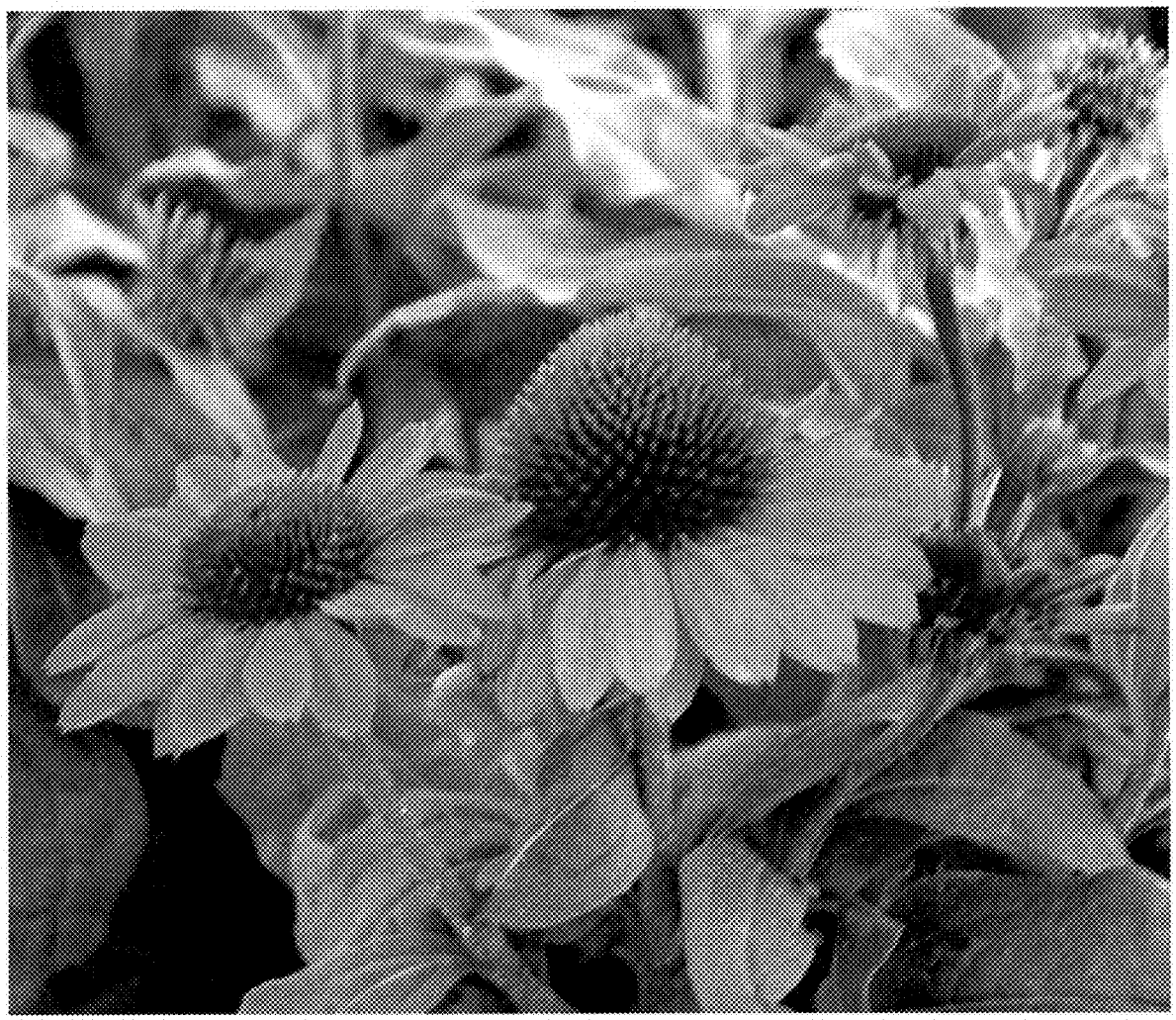
FIG. 2 shows a close up of some inflorescences at various stages.

The following description of *Echinacea* 'Knock 'em Red' is based on observations of two-year-old specimens grown in a full-sun trial garden with supplemental water and fertilizer in Zeeland, Michigan. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: The female or seed parent is the proprietary unreleased hybrid 17-7-x and the male or pollen parent is the proprietary unreleased hybrid 17-7-xx.

Plant habit: Multi-stemmed, heavily-branched, hardy herbaceous perennial, flowering to about 60 cm tall and 60 cm wide;

Growth rate: Vigorous, finishing in 3.8-liter containers in about 2 months during the summer;

Roots: Cream-colored, finely branched; color nearest RHS NN155B depending on soil;

Foliage: Alternate; lanceolate; acute apex; attenuate base; margin serrulate, micro-ciliolate; strigose abaxial and adaxial; to about 22 cm long and 9 cm wide decreasing distally, average about 9.5 cm long and 3.8 cm wide; variegation absent;

Leaf color: Young leaves adaxial nearest RHS NN137C, abaxial between RHS 147B and RHS 147C; mature leaves adaxial nearest NN137A, abaxial nearest RHS 147B; variegation absent;

Foliage fragrance: Lightly herbal;

Venation: Pinnately three-nerved and reticulate; abaxial midrib and veins costate; glabrous adaxial, hirsutulous abaxial;

Vein color: Adaxial basal midrib and basal primary veins between RHS 193A and RHS 145C, distally nearest RHS NN137A; abaxial proximal midrib between RHS 145B and RHS 146D, distal midrib and primary veins nearest RHS 137B secondary veins nearest RHS NN137B;

Petiole: Concavo-convex; glabrous adaxial; hirsutulous abaxial; to about 14 cm long and 12 mm wide at the semi-clasping base and 3 mm wide in middle of lowest leaves and decreasing to nearly sessile distally;

Petiole color: Adaxial base nearest RHS 71A, abaxial base nearest RHS 186A, adaxial midrib between nearest RHS 186A and the margins 145D and RHS 146D; abaxial midrib between RHS 145D and RHS 145C, and the abaxial margins nearest RHS NN137C;

Peduncle: Densely puberulent to strigillose; cylindrical; strong stiff; to about 14 cm long and 7 mm diameter at base above highest leaf; quantity per plant about eight; flowering in upper 39 cm;

Peduncle color: Variable, nearest RHS 176B with a faint blush of nearest RHS 187A to nearest RHS 146D;

Branches: Cylindrical, puberulent to strigillose; tightly angled to main stem to about 60° above horizontal: to about 24.5 cm long and 4 mm diameter; color in high light nearest RHS 176B with a faint blush of nearest RHS 187A to nearest RHS 146D in portion protected from high light exposure;

Inflorescence: Bracteate head, aggregate of achene; with single whorl of distinct, imbricate, ligulate, ray florets and central disk florets in a pappus; flowering mid-summer to fall frost; initial inflorescence largest, to about 10.5 cm wide and 4.5 cm tall, average about 9.0 cm wide and 4 cm tall, with cones 4.5 cm across and 3.5 cm tall;

Inflorescence fragrance: Lightly sweet;

Flower persistence: Ray florets remaining affective in color for 10 to 14 days depending on temperatures, cone persistent and effective through drying on plant into winter;

Involucre: With numerous bracts; to about 86 per inflorescence in 3 to 4 whorls; reflexed downward toward peduncle;

Involucre bracts: Linear; narrowly acute apex; truncate base; micro-ciliolate margin; adaxial glabrous and matte; abaxial micro-puberulent; reflexed greater than 90 degrees; to about 14 mm long and 3.5 mm across; average about 13 mm long and 3 mm across at base;

Involucre bract color: Adaxial center nearest RHS 138B, margins nearest RHS NN137B, with a variable moderate to light blush of nearest RHS 187A; abaxial center and margin between RHS 138A and RHS 138B;

Inflorescence buds with ray florets vertical and still enrolled: About 40 mm across and 28 mm tall; ray floret color adaxial nearest RHS 44B and abaxial between RHS 51A and RHS 53D, with spines nearest RHS 187B;

Ray florets: Zygomorphic; arrangement in single whorl, broadly-overlapping, typically imbricate; lanceolate; apex emarginated with typically two notches to 2 mm deep; base cuneate into claw; margin entire; adaxial and abaxial matte and glabrous; 18 to 20 per inflorescence, typically more with initial flowers; flat; opening and staying nearly horizontal until just before dropping; sterile; ligule to 47 mm long and 16 mm wide near middle, average size 44 mm long, 15 mm wide tapering to 2 mm wide in basal 4 mm; typically two thickened veins raised; twisting or enrolling absent;

Ray ligule color: When first horizontal-adaxial blade and claw nearest RHS 44A, abaxial blade between RHS 54B and RHS 54C with the claw between RHS 157A and RHS 193B; when flower mature-adaxial blade nearest RHS 53A, abaxial blade between RHS 60C and RHS 64D with claw nearest RHS 146D; before dehiscence-adaxial blade between RHS 53A and RHS 60A and claw nearest N187A, abaxial nearest RHS 59C and claw nearest RHS 148B;

Disc florets: About 300 to 600 per head; actinomorphic; perfect; synandrous; produced in raised dome, to about 3.5 cm across and 3 cm tall; individual florets to about 11 mm long to exserted style and 2 mm diameter;

Corolla: Connate forming tube; to about 6 mm long and 1.5 mm wide, near disc center florets about 7 mm long and 1.5 mm wide; fused in basal 6 mm, free in distal 1 mm; individual tepals about 0.7 mm wide at fusion; acute apex; entire margin; adaxial and abaxial surfaces slightly lustrous;

Corolla tube color: Adaxial and abaxial nearest RHS 148B with proximal and distal ends nearest RHS N186C;

Androecium: Only observed in disk florets; five; synandrous;

Staminal column: Five connate stamens; about 1 mm diameter and 5 mm long;

Anthers: Connate; longitudinal; about 3.5 mm long and 1 mm diameter; color nearest RHS 200A;

Filaments: Five; attached to column base; thin, about 0.1 mm diameter and about 1.5 mm long; color nearest RHS 155D;

15 Pollen: Globose, abundant, less 0.1 mm in diameter, RHS 17B;

Gynoecium: Single; to about 8 mm long;

Style: About 5 mm long and 0.2 mm diameter; color nearest RHS 145D;

Stigma: Bifid; reflexed about 180°; about 2 mm long and 0.2 mm diameter; color nearest RHS N187A;

Seed: Achene; apex truncate to funiculus, with four main pappus; about 5 mm long and 2 mm across; funiculus about 1 mm across and 0.5 mm long;

Pappus: Fimbriate; 1 mm long and 2 mm across;

Seed color: Between RHS 199B and RHSN 199A;

Receptacle spines: One per disk florets; acicular; apex acute; base attenuate; lustrous; glabrous; to 15 mm long and 3 mm across near middle;

Spine color: Adaxial and abaxial base nearest RHS 155C, middle portion between RHS 144A and RHS 146D, distally nearest RHS N172B and apical 1 mm nearest RHS 187A; becoming nearest RHS 183A with flower maturity and drying to nearest RHS 200A;

Culture and performance: The new plant performs well and with stiff stems remains upright even when exposed to heavy rains and high winds.

Disease and pest resistance: The new plant has not been shown to have any disease or pest resistance or susceptibility beyond that common to Coneflower plants.

I claim:

1. A new and distinct ornamental cultivar of *Echinacea* plant named 'Knock 'em Red' as herein described and illustrated.

* * * * *